United States Patent
Takagi et al.

(10) Patent No.: US 6,762,058 B2
(45) Date of Patent: Jul. 13, 2004

(54) EXAMINATION METHOD OF BUFFER CAPACITY OF SALIVA AND EXAMINATION INSTRUMENT OF BUFFER CAPACITY OF SALIVA

(75) Inventors: Kazuhiro Takagi, Tokyo (JP); Junichi Okada, Tokyo (JP); Yoshiko Watanabe, Tokyo (JP)

(73) Assignee: GC Corporation, Tokyo (JP)

( * ) Notice: Subject to any disclaimer, the term of this patent is extended or adjusted under 35 U.S.C. 154(b) by 106 days.

(21) Appl. No.: 10/131,190

(22) Filed: Apr. 25, 2002

(65) Prior Publication Data

US 2002/0182742 A1 Dec. 5, 2002

(30) Foreign Application Priority Data

Apr. 27, 2001 (JP) ........................................ 2001-132278

(51) Int. Cl.[7] .......................... G01N 31/16; G01N 31/22
(52) U.S. Cl. ........................ 436/163; 436/162; 436/164; 436/169
(58) Field of Search .................................. 436/162, 169, 436/163, 164; 422/56, 57; 116/201, 206

(56) References Cited

U.S. PATENT DOCUMENTS

2003/0059947 A1 * 3/2003 Takagi et al. ................ 436/163

FOREIGN PATENT DOCUMENTS

JP          57175129 A    * 10/1982

OTHER PUBLICATIONS

CAPLUS AN 1999:775558, Bardow et al., Archives of Oral Biology (2000), 45(1), 1–12.*
D. Ericson, et al., Biosis 'Online!, vol. 97, No. 5, 1 page, AN–PREV199089002027, XP–002232368, "Simplified Method to Estimate Salivary Buffer Capacity", 1989.
S Wikner, et al., Medline 'Online!, vol. 9, No. 2, 1page, AN–NLM3859942, XP–002232369, "A Clinical Evaluation of the Ability of the Dentobuff Method to Estimate Buffer Capacity of Saliva", 1985.
G. Frostell, Medline 'Online!, vol. 4, No. 3, 1page, AN–NLM6933707, XP–002232370, "A Colourimetric Screening Test for Evaluation of the Buffer Capacity of Saliva", 1980.

* cited by examiner

Primary Examiner—Jan M. Ludlow
(74) Attorney, Agent, or Firm—Oblon, Spivak, McClelland, Maier & Neustadt, P.C.

(57) ABSTRACT

To provide an examination method of buffer capacity of saliva and an examination instrument of buffer capacity of saliva, by which the buffer capacity of saliva of a subject can be examined simply without being influenced by an amount of saliva and preciously without being influenced by the subjectivity of an examiner, an end portion of an absorptive material in a predetermined shape, containing a pH indicator at least having one or more color transition range of pH 4.0 to 7.0 and an acid, is dipped in saliva to allow the saliva to penetrate into the absorptive material, and a buffer capacity of the saliva is examined from a distance where a color to be exhibited by the pH indicator has changed by the penetrated saliva from a predetermined place of the absorptive material and a distance where the saliva has penetrated from a predetermined place of the absorptive material.

26 Claims, No Drawings

EXAMINATION METHOD OF BUFFER CAPACITY OF SALIVA AND EXAMINATION INSTRUMENT OF BUFFER CAPACITY OF SALIVA

BACKGROUND OF THE INVENTION

1. Field of the Invention

The present invention relates to an examination method of buffer capacity of saliva and an examination instrument of buffer capacity of saliva, by which the buffer capacity of saliva of a subject can be examined simply without being influenced by an amount of saliva and preciously without being influenced by the subjectivity of an examiner.

2. Description of the Conventional Art

The forming and progress of dental caries are made in the following steps. That is, when demineralization wherein acids produced by the metabolism of hydrocarbons by bacteria in an oral cavity elute calcium ions and phosphate ions in teeth, and remineralization that is a phenomenon wherein the calcium ions and phosphate ions are again taken into the teeth, repeatedly function over a long period of time, a balance between the both is broken, and the environment is inclined to the demineralization side for a long time, whereby the dental caries is formed and proceeds. The role of saliva includes not only a function to supply calcium ions and phosphate ions present in saliva to teeth but also a buffer capacity to neutralize acids produced by the metabolism of hydrocarbons by bacteria in an oral cavity, thereby preventing demineralization. Since there are observed differences in the buffer capacity of saliva against the acids individually, for making a guide for stopping the forming and progress of the dental caries, it is necessary to obtain objective information individually regarding the buffer capacity of saliva.

The buffer capacity of saliva is regulated mainly by the following three buffer functions: a function by the correlation between carbonic acid and a bicarbonate, a function by phosphates, and a function by proteins. Of these, the function by the correlation between carbonic acid and a bicarbonate is the most important, which is based on an equilibrium relation between carbonic acid and the bicarbonate. When an acid is added, the bicarbonate releases carbonic acid as a weak acid. This carbonic acid is rapidly decomposed into water and carbon dioxide, and then is liberated from the solution. In contrast to many buffering agents, this mechanism results in not accumulation of a weak acid but complete elimination of the acid. That is, in order that the buffer capacity of saliva based on the equilibrium relation between carbonic acid and the bicarbonate is maintained, it is considered that a sufficient amount of the bicarbonate for eliminating a large amount of the acid is needed. Further, it is already confirmed that the variation of the bicarbonate in saliva appears in a pH change.

Accordingly, for examining the buffer capacity of saliva, the evaluation of the amount of the bicarbonate through titration using an acid is the most confident, and its standard method at a laboratory level is the Ericsson method (see Ericsson Y.; "Clinical investigations of the salivary buffering action", *Acta. Odontol. Scand.*, 17:311–65 (1959)). This Ericsson method is a method in which a certain amount of hydrochloric acid is added to collected saliva, the mixture is stirred for a certain period of time while subjecting to a treatment for avoiding bubbling and inclusion of carbon dioxide, and then, the ultimate pH is measured using electrodes. However, since this method requires a complicated operation and a specific device, it is not generally diffused.

Thus, as a method for examining the buffer capacity of saliva more simply, employed is a method in which saliva is dropped to a paper having been previously immersed with a weak acid and a pH indicator and dried using a dropping pipette such that the saliva covers the whole of the paper; and after the lapse of five minutes, the pH that has increased by the saliva is determined by comparing a color of the portion to which the saliva has been added dropped with a color sample at a known pH, whereby the buffer capacity of saliva is examined according to the three grades (low, medium and high) (see Takashi KUMAGAYA, et al., *Clinical Cardiology*, 130–31, published by Ishiyaku Publishers, Inc.). According to this method, though it is possible to examine the buffer capacity of saliva simply, there was involved a problem that a dispersion in the amount of the saliva to be dropped, or a variation in the color determination by an examiner, is large so that errors are likely caused.

SUMMARY OF THE INVENTION

The present invention is aimed to overcome the above-described problems of the conventional art techniques and to provide an examination method of buffer capacity of saliva and an examination instrument of buffer capacity of saliva, by which the buffer capacity of saliva of a subject can be examined simply without being influenced by an amount of saliva and preciously without being influenced by the subjectivity of an examiner.

In order to achieve the above-described aim, we, the present inventors made extensive and intensive investigations. As a result, they have found the following matters. That is, when a pH indicator and an acid are previously contained in an absorptive material into which a liquid penetrates, and one end of the absorptive material is dipped in saliva, during a step when the saliva penetrates into the absorptive material, a buffer capacity functions against the acid previously contained in the absorptive material by the action of carbonic acid and a bicarbonate in the saliva, whereby the saliva continues to exhibit neutrality as in an oral cavity at the initial stage. However, when the saliva further penetrates into the absorptive material and continues to be exposed to the acid, the saliva loses the buffer capacity, so that it can no longer exhibit the neutrality. Utilizing this matter, when one having a predetermined shape is prepared as the absorptive material in which a pH indicator and an acid have been previously contained, and an amount of saliva having penetrated into this absorptive material and an amount of saliva having changed the color to be exhibited by the pH indicator by the penetrated saliva are measured from a distance where the color to be exhibited by the pH indicator has changed by the penetrated saliva from a predetermined place of the absorptive material and a distance where the saliva has penetrated from a predetermined place of the absorptive material, the buffer capacity of the individual saliva can be examined simply without being influenced by an amount of saliva and preciously without being influenced by the subjectivity of an examiner. Thus, the present invention has been completed.

Specifically, the invention relates to an examination method of buffer capacity of saliva comprising dipping an end portion of an absorptive material in a predetermined shape, containing a pH indicator at least having one or more color transition range of pH 4.0 to 7.0 and an acid, in saliva to allow the saliva to penetrate into the absorptive material, and examining a buffer capacity of the saliva from a distance where a color to be exhibited by the pH indicator has changed by the penetrated saliva from a predetermined place of the absorptive material and a distance where the saliva has penetrated from a predetermined place of the absorptive material; and to an examination instrument of buffer capacity of saliva comprising an absorptive material in a predetermined shape, containing a pH indicator at least having one or more color transition range of pH 4.0 to 7.0 and an acid.

Further, it has been found that the absorptive material is preferably an absorptive material having a property such that, when the absorptive material with a constant lateral cross-sectional area is made to stand upright to a water surface and its end portion of 10 mm is dipped in water, a penetration distance of water is 10 to 200 mm under the conditions at a temperature of 23° C. and at a humidity of 50% for 5 minutes; and that the acid contained in the absorptive material preferably has a normality of 0.005 to 5.0 N.

DESCRIPTION OF THE PREFERRED EMBODIMENTS

The absorptive material that is used in the present invention is not particularly limited, so far as it can contain the pH indicator and the acid and can absorb saliva therein. As a raw material of the absorptive material, papers such as filter paper, blotting paper, and paper towel are the most preferable. Besides, suitable are cloths and non-woven fabrics made of, e.g., absorbent cotton, quartz wool, glass wool, wool, silk, cotton, linen, acrylic fibers, rayon, nylon, nitrocellulose, cellulose acetate, regenerated cellulose, glass fibers, etc. Also, employable are solid moldings of dextran, mutan, levan, cellulose powder, etc.

With respect to the absorptive material, in the case where a lateral cross-sectional area thereof is constant, when it is made to stand upright to a water surface, and its end portion of 10 mm is dipped in water, a penetration distance of water expressed by a length of water rising within the absorptive material due to capillarity is preferably 10 to 200 mm, and more preferably from 20 to 100 mm, under the conditions at a temperature of 23° C. and at a humidity of 50% for 5 minutes. This is because when the penetration distance of water to the absorptive material is less than 10 mm for 5 minutes or exceeds 200 mm for 5 minutes, the precious examination of the buffer capacity tends to become difficult.

The shape of the absorptive material that is used in the present invention includes various forms such as a strip-like form, a cylindrical form, a string-like form, a square pillar-like form, and a conical form. For example, when the absorptive material is a paper material, employable are a strip-like form having a thickness of 0.1 to 2.0 mm, a width of about 10 mm, and a length of about 70 mm and a cylindrical form having a diameter of 0.2 to 10 mm and a length of about 70 mm; and when the absorptive material is a material such as cellulose powders filled in a glass tube, etc., employable is a form having an inner diameter of 1 to 10 mm and a length of about 70 mm. In these forms, it is preferred that the absorptive material or a container having the absorptive material filled therein is provided with graduations or numeral values at certain intervals of, for example, 1 mm.

The acid that is contained in the absorptive material preferably has a normality of 0.005 to 5.0 N, and examples of the acid that can be used are usual acids such as hydrochloric acid, sulfuric acid, nitric acid, nitrous acid, lactic acid, citric acid, oxalic acid, benzoic acid, formic acid, salicylic acid, tartaric acid, acetic acid, dichloroacetic acid, trichloroacetic acid, pyruvic acid, boric acid, maleic acid, hyaluronic acid, acrylic acid, adipic acid, uric acid, phthalic acid, docosahexanoic acid, glutamic acid, alginic acid, ascorbic acid, aspartic acid, folic acid, and malic acid. Of these, preferred are hydrochloric acid, nitrous acid and lactic acid because these acids give rise to stable examination results and are easily obtainable. When the normality of the acid is less than 0.005 N, it is necessary to absorb a large amount of the saliva to the absorptive material by, for example, increasing the length of the absorptive material, in order to examine the general buffer capacity of saliva, and hence, such is not practically useful. On the other hand, when the normality of the acid exceeds 5 N, the precision of the examination tends to be inferior, possibly resulting in an error. These acids are dissolved in water or a solution of an alcohol, etc. and then impregnated in the absorptive material by means of immersion, spraying, etc., followed by drying and use.

The pH indicator that is used in the present invention is not particularly limited, so far as it at least has one or more color transition range of pH 4.0 to 7.0. For example, 2,5-dinitrophenol (color transition range: from 4.0 to 5.8), Methyl Red (color transition range: from 4.4 to 6.2), p-nitrophenol (color transition range: from 5.0 to 7.0), azolitmin (color transition range: from 5.0 to 8.0), Bromocresol Purple (color transition range: from 5.2 to 6.8) Bromophenol Red (color transition range: from 5.2 to 6.8), Chlorophenol Red (color transition range: from 5.2 to 6.8), Bromothymol Blue (color transition range: from 6.0 to 7.6), and the like are preferred as the pH indicator because they have a color transition range of pH 4.0 to 7.0. Further, these pH indicators can be used in combination with Phenol Red (color transition range: from 6.4 to 8.0), m-nitrophenol (color transition range: from 6.4 to 8.8), Neutral Red (color transition range: from 6.8 to 8.0), rosolic acid (color transition range: from 6.8 to 8.0), or the like. Similar to the acid, these pH indicators are dissolved in water or a solution, etc. and then impregnated in the absorptive material by means of immersion, spraying, etc., followed by drying and use.

In practicing the examination method of buffer capacity of saliva according to the present invention, an end portion of the absorptive material is dipped in extracted saliva. At this time, it is preferred that saliva from which impurities and viscous substances such as mucin have been removed by a filtration treatment of passing it through a filter or other means is used as the saliva. Further, it is preferred that the end portion of the absorptive material to be dipped in the extracted saliva is within a range up to about 20 mm from the tip thereof. The saliva penetrates into the absorptive material due to capillarity. During this step, a buffer capacity functions to the acid previously contained in the absorptive material by the action of carbonic acid and a bicarbonate in the saliva, whereby the saliva continues to exhibit neutrality as in an oral cavity at the initial stage. However, when the saliva further rises in the absorptive material and continues to be exposed to the acid, the saliva loses the buffer capacity, so that it can no longer exhibit the neutrality. In the present invention, the examination is effected from a ratio of an amount of the saliva having penetrated into this absorptive material to an amount of the saliva having changed the color of the pH indicator to be exhibited by the penetrated saliva. However, it is very complicated to obtain these amounts. Therefore, the measurement is effected by a distance where the color to be exhibited by the pH indicator has changed by the penetrated saliva from a predetermined place of the absorptive material and a distance where the saliva has penetrated from a predetermined place of the absorptive material. In other words, a relation between the penetration amount of the saliva of the used absorptive material and the distance from the predetermined place of the absorptive material at that time is unequivocally determined. Accordingly, if this relation is previously grasped, the ratio of the amount of the saliva having penetrated into this absorptive material to the amount of the saliva having changed the color of the pH indicator to be exhibited by the penetrated saliva can be obtained from the distance where the color to be exhibited by the pH indicator has changed by the penetrated saliva from the predetermined place of the absorptive material and the distance where the saliva has penetrated from the predetermined place of the absorptive material. In this case, for example, at the time when the saliva has penetrated into the whole of the absorptive material, one may be required to measure only the distance where the color to be exhibited by the pH indicator has changed by the penetrated saliva from the predetermined place of the absorptive material. That is, one may be required to measure only one length but not two lengths, and hence, the measurement is simple. The term "predetermined place of the absorptive material" as referred to in the specification and claims of the present invention means a position previously marked in the vicinity of the end portion of the absorptive material, or a tip of the end portion, in order to indicate the position at which the absorptive material is to be dipped. At this time, in the case where the examination is carried out using saliva having a standard buffer capacity as previously measured, the distance where the color to be exhibited by the pH indicator has changed may be shown by numerical values, etc. in a separate table. Further, it is more preferred that the predetermined place of the absorptive material is expressed by a dot or a zone on the absorptive material for the examination instrument of buffer capacity of saliva or its container.

The invention will be further described with reference to the following Examples, but it should not be construed that the invention is limited thereto.

EXAMPLE 1

A strip-like quantitative filter paper No. 41 (made by Whatman plc) having a width of 10 mm, a thickness of 0.2 mm and a length of 60 mm as an absorptive material was dipped and immersed in a mixed solution of 0.02 N hydrochloric acid and 1 mg/L of Bromothymol Blue, and then dried to prepare an examination instrument of buffer capacity of saliva. This examination instrument of buffer capacity of saliva was acidic and colored yellow. When an end portion of 5 mm of this absorptive material was dipped in saliva having been filtered through an AP Filter Ap15 Type (made by Millipore Corp.), the color of the absorptive material gradually changed to blue from the end portion of the absorptive material dipped in the saliva. Further, when the saliva had penetrated in the whole of the absorptive material, a portion where the saliva that had continued to be exposed to the acid and lost the buffer capacity penetrated was kept yellow. At this time, a distance from the tip of the absorptive material dipped in the saliva to an interface between the blue color and the yellow color was measured by three examiners A to C individually. The results obtained are shown in Table 1. Incidentally, a penetration distance of water to the absorptive material used in Example 1 was 42.3 mm under the conditions at a temperature of 23° C. and at a humidity of 50% for 5 minutes. Further, when an end portion of 5 mm of the absorptive material was dipped in an aqueous sodium bicarbonate solution having a known concentration, and the aqueous sodium bicarbonate solution penetrated in the whole of the absorptive material, a distance from the tip of the absorptive material dipped in the aqueous sodium bicarbonate solution to an interface between the blue color and the yellow color was measured. The results obtained are shown in Table 2.

EXAMPLE 2

A quantitative filter paper No. 41 (made by Whatman plc) processed in a cylindrical form having a diameter of 1 mm and a length of 60 mm as an absorptive material was dipped and immersed in a mixed solution of 0.02 N hydrochloric acid and 1 mg/L of Bromothymol Blue, and then dried to prepare an examination instrument of buffer capacity of saliva. This examination instrument of buffer capacity of saliva was acidic and colored yellow. When an end portion of 5 mm of this absorptive material was dipped in saliva having been filtered through an AP Filter Ap15 Type (made by Millipore Corp.), the color of the absorptive material gradually changed to blue from the end portion of the absorptive material dipped in the saliva. Further, when the saliva had penetrated in the whole of the absorptive material, a portion where the saliva that had continued to be exposed to the acid and lost the buffer capacity penetrated was kept yellow. At this time, a distance from the tip of the absorptive material dipped in the saliva to an interface between the blue color and the yellow color was measured by three examiners A to C individually. The results obtained are shown in Table 1. Incidentally, a penetration distance of water to the absorptive material used in Example 2 was 30.1 mm under the conditions at a temperature of 23° C. and at a humidity of 50% for 5 minutes. Further, when an end portion of 5 mm of the absorptive material was dipped in an aqueous sodium bicarbonate solution having a known concentration, and the aqueous sodium bicarbonate solution penetrated in the whole of the absorptive material, a distance from the tip of the absorptive material dipped in the aqueous sodium bicarbonate solution to an interface between the blue color and the yellow color was measured. The results obtained are shown in Table 2.

EXAMPLE 3

A strip-like chromatographic filter paper No. 51A (made by Advantec Mfs. Inc.) having a width of 10 mm, a thickness of 0.2 mm and a length of 60 mm as an absorptive material was dipped and immersed in a mixed solution of 0.2 N lactic acid and 1 mg/L of Bromothymol Blue, and then dried to prepare an examination instrument of buffer capacity of saliva. This examination instrument of buffer capacity of saliva was acidic and colored yellow. When an end portion of 5 mm of this absorptive material was dipped in saliva having been filtered through an AP Filter Ap15 Type (made by Millipore Corp.), the color of the absorptive material gradually changed to blue from the end portion of the absorptive material dipped in the saliva. Further, when the saliva had penetrated in the whole of the absorptive material, a portion where the saliva that had continued to be exposed to the acid and lost the buffer capacity penetrated was kept yellow. At this time, a distance from the tip of the absorptive material dipped in the saliva to an interface between the blue color and the yellow color was measured by three examiners A to C individually. The results obtained are shown in Table 1. Incidentally, a penetration distance of water to the absorptive material used in Example 3 was 32.0 mm under the conditions at a temperature of 23° C. and at a humidity of 50% for 5 minutes. Further, when an end portion of 5 mm of the absorptive material was dipped in an aqueous sodium bicarbonate solution having a known concentration, and the aqueous sodium bicarbonate solution penetrated in the whole of the absorptive material, a distance from the tip of the absorptive material dipped in the aqueous sodium bicarbonate solution to an interface between the blue color and the yellow color was measured. The results obtained are shown in Table 2.

EXAMPLE 4

A quantitative filter paper No. 41 (made by Whatman plc) processed in a cylindrical form having a diameter of 1 mm and a length of 60 mm as an absorptive material was dipped and immersed in a mixed solution of 0.2 N lactic acid and 1 mg/L of Bromothymol Blue, and then dried to prepare an examination instrument of buffer capacity of saliva. This examination instrument of buffer capacity of saliva was acidic and colored yellow. When an end portion of 5 mm of this absorptive material was dipped in saliva having been filtered through an AP Filter Ap15 Type (made by Millipore Corp.), the color of the absorptive material gradually changed to blue from the end portion of the absorptive material dipped in the saliva. Further, when the saliva had penetrated in the whole of the absorptive material, a portion where the saliva that had continued to be exposed to the acid and lost the buffer capacity penetrated was kept yellow. At this time, a distance from the tip of the absorptive material dipped in the saliva to an interface between the blue color and the yellow color was measured by three examiners A to C individually. The results obtained are shown in Table 1. Incidentally, a penetration distance of water to the absorptive material used in Example 4 was 38.3 mm under the conditions at a temperature of 23° C. and at a humidity of 50% for 5 minutes. Further, when an end portion of 5 mm of the absorptive material was dipped in an aqueous sodium bicarbonate solution having a known concentration, and the aqueous sodium bicarbonate solution penetrated in the whole of the absorptive material, a distance from the tip of the absorptive material dipped in the aqueous sodium bicarbonate solution to an interface between the blue color and the yellow color was measured. The results obtained are shown in Table 2.

TABLE 1

| Examiner | Example 1 (mm) | Example 2 (mm) | Example 3 (mm) | Example 4 (mm) |
|---|---|---|---|---|
| A | 43.0 | 44.5 | 44.0 | 42.0 |
| B | 43.3 | 44.4 | 43.7 | 43.0 |
| C | 42.8 | 44.9 | 44.1 | 42.3 |

TABLE 2

| Concentration of sodium bicarbonate solution (mM) | Example 1 (mm) | Example 2 (mm) | Example 3 (mm) | Example 4 (mm) |
|---|---|---|---|---|
| 10 | 37.2 | 36.9 | 36.8 | 37.4 |
| 20 | 40.2 | 40.9 | 39.7 | 39.5 |
| 30 | 43.8 | 44.0 | 42.8 | 43.6 |
| 40 | 46.1 | 47.1 | 46.9 | 46.7 |
| 50 | 48.7 | 49.2 | 49.1 | 48.8 |

As is evident from Table 1, it can be confirmed that in Examples 1 to 4, a variation in the examination results by the examiners is small. Further, as is evident from Table 2, it can be confirmed that in Examples 1 to 4, there is a proportional relation between the concentration of the bicarbonate and the distance to be measured. Accordingly, the examination method of buffer capacity using the examination instrument of buffer capacity according to the present invention enabled to examine the buffer capacity of saliva of a subject simply and preciously without being influenced by the subjectivity of an examiner.

As described above in detail, the examination method of buffer capacity and the examination instrument of buffer capacity according to the present invention enable one to carry out an examination of saliva necessary for making a guide for stopping the forming and progress of dental caries of a subject simply without being influenced by an amount of the saliva and preciously without being influenced by the subjectivity of an examiner. Accordingly, the present invention is greatly valuable in contribution to the dental remedy field. In addition, utilizing this principle, the present invention is applicable to blood and aqueous solutions, and is greatly valuable in contribution to not only the dental remedy field but also various fields including all medical treatments, examination of water, and preparation of reagents.

While the invention has been described in detail and with reference to specific embodiments thereof, it will be apparent to one skilled in the art that various changes and modifications can be made therein without departing from the spirit and scope thereof.

What is claimed is:

1. An examination method for determining the buffering capacity of saliva comprising:

dipping an end portion of an absorptive material containing a pH indicator which exhibits at least one color transition in the range of pH 4.0 to 7.0 and an acid, into saliva, allowing saliva to migrate into said absorptive material and into contact with said pH indicator from a predetermined place, and determining the buffering capacity of the saliva by comparing the migration distance of the saliva (fluid front) and the migration distance of a color change interface produced by contact of the saliva with the pH indicator in the absorptive material.

2. The method of claim 1, wherein said absorptive material has a predetermined shape.

3. The method of claim 1, wherein said absorptive material is in a strip-like form.

4. The method of claim 1, wherein said absorptive material is in a cylindrical form.

5. The method of claim 1, wherein said absorptive material is in a string-like form, a square pillar-like form, or a conical form.

6. The method of claim 1, wherein said absorptive material is selected from the group consisting of filter paper, blotting paper, or paper towel.

7. The method of claim 1, wherein said absorptive material is a cloth or non-woven fabric made of cotton, linen, wool or silk.

8. The method of claim 1, wherein said absorptive material is a cloth or non-woven fabric made of acrylic fibers, rayon, nylon, nitrocellulose, cellulose acetate or regenerated cellulose.

9. The method of claim 1, wherein said absorptive material is a cloth or non-woven fabric made of quartz wool, glass wool, or glass fibers.

10. The method of claim 1, wherein said absorptive material is a solid molding of dextran, mutan, levan, or cellulose powder.

11. The method of claim 1, Wherein said pH indicator is 2, 5-dinitrophenol.

12. The method of claim 1, wherein said pH indicator is Methyl Red.

13. The method of claim 1, wherein said pH indicator is p-nitrophenol.

14. The method of claim 1, wherein said pH indicator is azolitmin.

15. The method of claim 1, wherein said pH indicator is Bromocresol Purple.

16. The method of claim 1, wherein said pH indicator is Bromophenol Red.

17. The method of claim 1, wherein said pH indicator is Chlorophenol Red.

18. The method of claim 1, wherein said pH indicator is Bromophenol Blue.

19. The method of claim 1, wherein the normality of the acid in said absorptive material ranges from 0.005 to 5N.

20. The method of claim 1, wherein said acid is hydrochloric acid.

21. The method of claim 1, wherein said acid is nitrous acid.

22. The method of claim 1, wherein said acid is lactic acid.

23. The method of claim 1, wherein said saliva has had impurities and viscous substances removed from it.

24. The method of claim 1, wherein the saliva (fluid front) has penetrated the whole of the absorptive material and only the distance of the color interface is measured.

25. The method of claim 1, wherein said predetermined place on said absorptive material is marked on the absorptive material.

26. The method of claim 1, wherein said predetermined place on said absorptive material is marked on the absorptive material as a dot or a zone.

* * * * *